United States Patent [19]

Heaton et al.

[11] Patent Number: 4,919,125

[45] Date of Patent: Apr. 24, 1990

[54] ANAESTHETIC VAPORISERS

[75] Inventors: Robert A. Heaton, Skipton; Stuart C. Leach, Ilkley; Joseph Hancock, Bagslate; Neil A. Sandy, Silsden, all of England

[73] Assignee: BOC Group PLC.

[21] Appl. No.: 341,984

[22] Filed: Apr. 24, 1989

[30] Foreign Application Priority Data

Apr. 27, 1988 [GB] United Kingdom ............... 8809897

[51] Int. Cl.$^5$ ............................................ A61M 15/00
[52] U.S. Cl. ........................... 128/203.14; 128/203.12; 128/203.25
[58] Field of Search ...................... 128/203.12, 203.23, 128/203.24, 203.26, 203.27, 203.14; 261/DIG. 65, 39.1, 63

[56] References Cited

U.S. PATENT DOCUMENTS

| | | | |
|---|---|---|---|
| 2,178,519 | 10/1939 | Gill | 261/63 |
| 3,192,924 | 7/1965 | Edmondson et al. | 261/39.1 |
| 3,836,129 | 9/1974 | Perelmutr et al. | 261/DIG. 65 |
| 4,017,566 | 4/1977 | Seidel | 128/203.14 |
| 4,059,657 | 11/1977 | Hay | 128/203.25 |
| 4,067,935 | 1/1978 | Jones et al. | 128/203.14 |
| 4,129,621 | 12/1978 | Jones et al. | 128/203.14 |
| 4,607,634 | 8/1986 | Clapham | 261/DIG. 65 |

FOREIGN PATENT DOCUMENTS 968054 8/1964 United Kingdom .
1224478 3/1971 United Kingdom .

OTHER PUBLICATIONS

Anaesthetic Equipment Physical Principles and Maintenance by C. S. Ward, pp. 57-58.

Primary Examiner—David A. Wiecking
Assistant Examiner—Aaron J. Lewis

[57] ABSTRACT

An anaesthetic vaporiser 1 the by-pass type includes a thermally responsive valve 52 in its second by-pass stream which valve 52 is located immediately below the sump 12 of the vaporiser. This offers the advantage that any difference in temperature between the valve 52 and liquid anaesthetic contained in the sump 12 is very small even when the liquid anaesthetic temperature is changing rapidly. Furthermore, the valve 52 is readily accessible for maintenance and calibration.

5 Claims, 4 Drawing Sheets

ANAESTHETIC VAPORISERS

BACKGROUND OF THE INVENTION

The present invention relates to anaesthetic vaporisers and in particular to anaesthetic vaporisers of the by-pass type. UK Patent No. 1224478, describes an anaesthetic vaporiser of the by-pass type in which a carrier gas such as oxygen, air or nitrous oxide is initially divided on entry to the vaporiser between a first stream which is directed towards the sump or vaporising chamber of the vaporiser to entrain vapour from a volatile liquid anaesthetic contained therein; and a second by-pass stream, the first and second streams subsequently re-combining prior to leaving the vaporiser for delivery to a patient.

In UK Patent No. 1224478, there is described a thermally controlled valve which is located in the second, by-pass stream. The function of the thermally controlled valve is to adjust the quantity of carrier gas in the by-pass stream. As the temperature of the vaporiser increases the resistance of the thermally controlled valve to the flow of the carrier gas through the by-pass stream decreases thereby allowing more carrier gas to pass through it, and on recombining with the first stream emerging from the vaporiser sump produces a gas mixture containing the same proportion of anaesthetic drug as it does at the initial temperature. By locating the thermally responsive valve in the second by-pass stream the following technical advantages accrue:

(a) Some volatile liquid anaesthetic agents are corrosive in the presence of water vapour which is know to be present in some medical gas supplies and placing the thermally responsive valve in the by-pass stream protects this very sensitive device from the effects of such corrosion.

(b) The sensitivity of the thermally responsive valve may be judged by the fact that a concentration change by a factor of 0.05 occurs with a valve movement of 0.0001". Even this movement is however, coarse by comparison with the smaller movement which would have to be controlled if the thermally responsive valve was located in the first stream of the vaporiser where the flow rate of gas is much lower.

(c) The anaesthetic agent HALOTHANE contains thymol as a stabiliser and this can be left by evaporation on operating surfaces. Siting the thermally responsive valve in the second by-pass stream means that this most sensitive component is protected from the effects of thymol build-up.

It is believed, that the beneficial technical effects of placing the thermally responsive valve in the second by-pass stream has resulted in the popularity of anaesthetic vaporisers embodying the features described in UK Patent 1224478 with the medical profession.

However, the thermally controlled valve described in UK Patent No. 1224478, is located at a position spaced from the vaporising chamber approximately in the middle of the vaporiser which gives rise to the following disadvantages:

(a) There is a time delay in the thermal response of the valve following any temperature change of the liquid anaesthetic agent in the sump of the vaporiser; and (b) The thermally responsive valve is relatively inaccessible for adjustment and maintenance purposes.

SUMMARY OF THE INVENTION

It is an aim of the present invention to provide an anaesthetic vaporiser of the by-pass type having a thermally responsive valve located in the second, by-pass stream immediately adjacent the base of the vaporiser sump and which is easily accessible for adjustment and maintenance purposes.

According to the present invention, an anaesthetic vaporiser of the by-pass type in which carrier gas is initially divided into a first stream passing through a vaporising chamber containing a volatile liquid anaesthetic agent thereby entraining vapour from the volatile liquid anaesthetic agent and a second by-pass stream; the two streams subsequently recombining prior to leaving the vaporiser for delivery to a patient, comprises a thermally responsive valve located in the second by-pass stream the vaporising chamber including a base made from a material having a high thermal conductivity, the thermally responsive valve being located immediately below the base in the normal orientation of the anaesthetic vaporiser.

BRIEF DESCRIPTION OF DRAWINGS

An embodiment of the invention will be described, by way of example, reference being made to the Figures of the accompanying diagrammatic drawings in which.

DESCRIPTION OF PREFERRED EMBODIMENT

Figure 1:
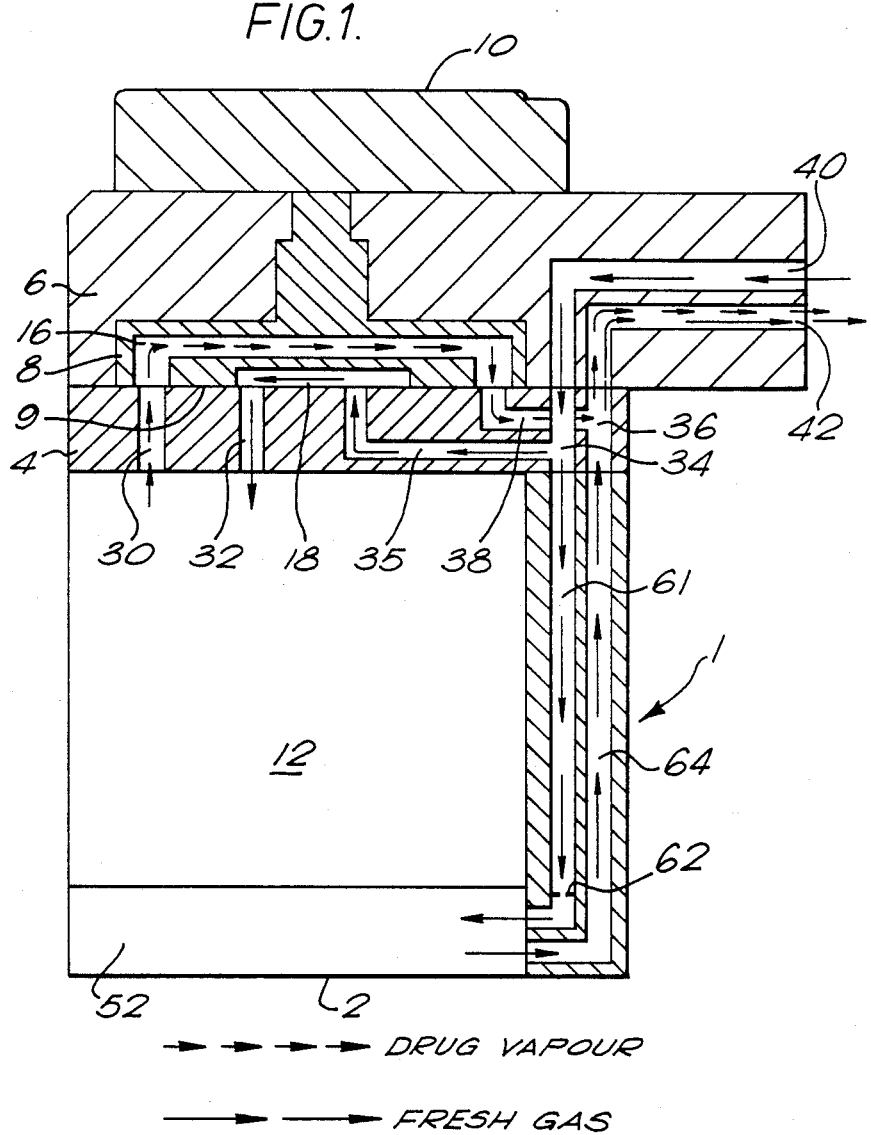
FIG. 1 is a side elevation partly in section of an anaesthetic vaporiser illustrating gas flow through the vaporiser when in its ON position.

As shown, an anaesthetic vaporiser 1 of the by-pass type includes a body casing having a base 2 and an upper closure plate 4. Mounted on the closure plate 4 is a guide part 6. A rotatable control valve 8 is located within the guide part 6. The control valve 8 can be rotated by means of a knob 10 attached thereto. Immediately below the closure plate 4 is a vaporising chamber or sump 12 for containing a volatile liquid anaesthetic agent and immediately below the vaporising chamber 12 there is located a thermally responsive valve 52.

Figure 3:
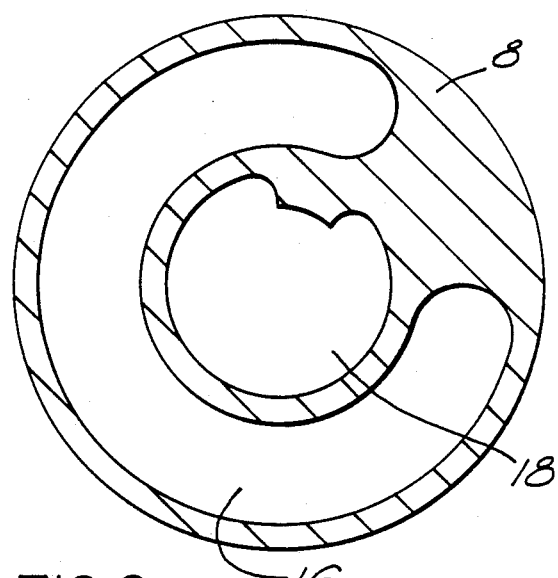
FIG. 3 is a sectional plan view from below of a facing surface of a control valve forming part of the anaesthetic vaporiser of FIGS. 1 and 2.

Referring in particular to FIG. 3, the control valve 8 on a facing surface 9, is formed with a control groove 16, and a by-pass recess 18.

The closure plate 4 has formed therein a plurality of passages namely passages 30, 32, 34, 35, 36 and 38.

The guide part 6 includes a carrier gas inlet 40 and a gas and vapour outlet 42.

Figure 4:
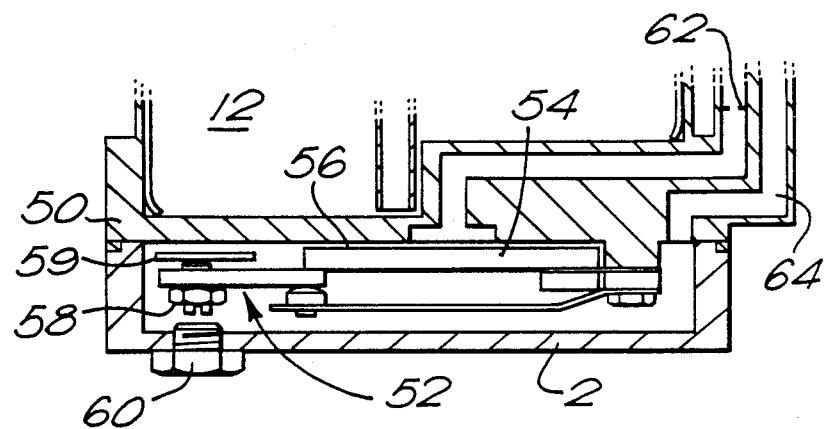
FIG. 4 is a detail of a thermally responsive valve forming part of the anaesthetic vaporiser of FIGS. 1 and 2.
Figure 5:
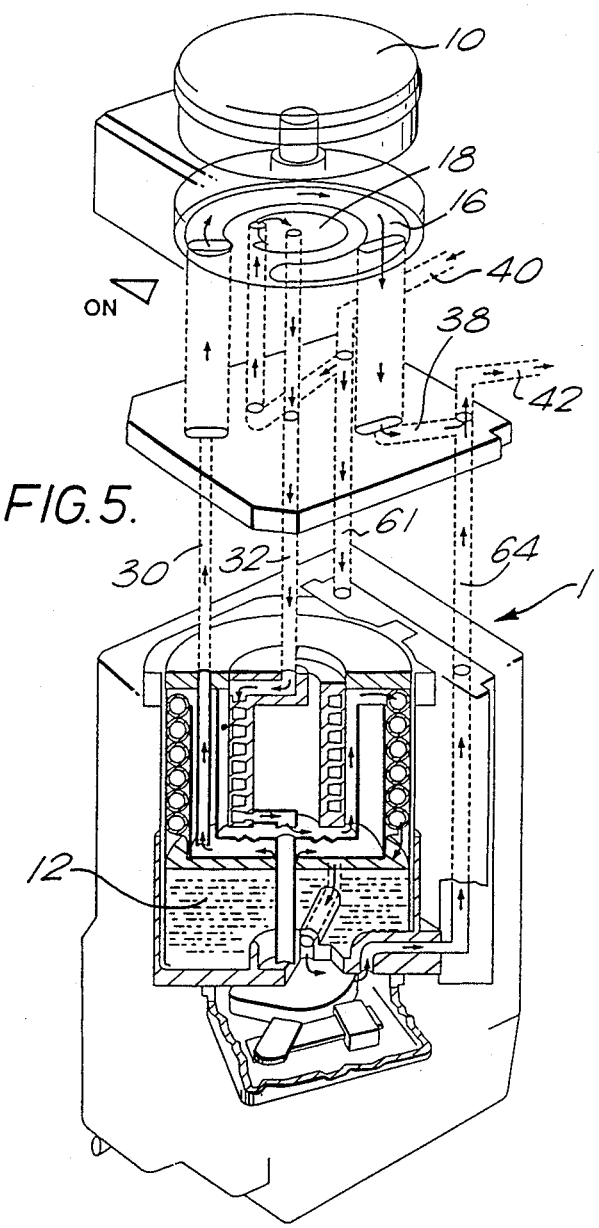
FIG. 5 is a schematic view of the complete anaesthetic vaporizer.

Referring in particular to FIG. 4, the sump or vaporiser chamber 12 has a thin walled base 50 made from material having a high thermal conductivity such as copper or a copper alloy. Immediately below (as shown) the base 50 is located a thermally responsive valve 52. The base 50 and a flapper 54 of the valve 52 define a passage 56 for the flow therethrough of the by-pass stream as will be described. Mounted on the valve 52 is an adjustment screw 58 and in alignment therewith a removable plug 60 threaded into the base 2 of the vaporiser 1. In the embodiment shown the screw 58 rests on a thermally responsive element 59, typically a bimetal device, which at a far end (not shown) is in contact with the base 50 in a manner known per se.

Figure 2:
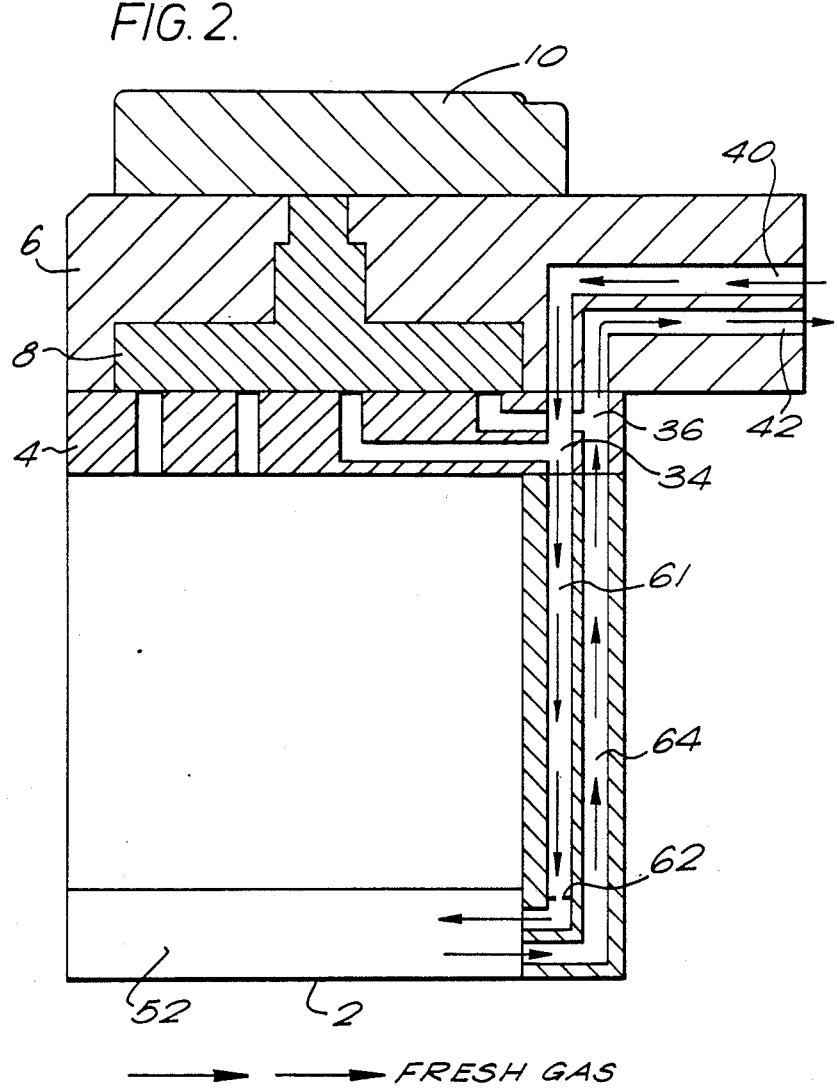
FIG. 2 is a view similar to FIG. 1 but showing the anaesthetic vaporiser in its OFF position.

When the vaporizer is mounted on or in an anaesthetic machine such that it is permanently connected to the carrier gas flow then, when the vaporizer is in its 'OFF' or zero output dial position as seen in FIG. 2, carrier gas enters inlet 40 where it is directed through passage 34 and channel 61 to the thermally responsive valve 52. From valve 52 the carrier gas flows through channel 64 and passage 36 to the outlet 42.

When the vaporiser is connected to the anaesthesia maching by a valve actuating mechanism such as that described in UK Patent 2 052 271 then at 'OFF' the gas connections to the machine are broken and no gas flows through the vaporizer.

When the vaporiser 1 is turned ON by rotating the knob 10 and hence the control valve 8, carrier gas enters the inlet 40 where it is directed to passage 34. At the passage 34, the carrier gas is divided into a first stream which passes into the sump or vaporising chamber 12 via passage 35, bypass recess 18 and passage 32, and a second by-pass stream which flows into channel 61.

The first stream entrains vapour of a volatile liquid anaesthetic contained in the sump area and the carrier gas and vapour mixture leaves the sump area to enter the passage 30 in the closure plate 4. From the passage 30 the gas, vapour mixture enters the control groove 16 in the facing surface 9 and hence flows into the passage 38.

The second, by-pass stream as previously described flows along the passage 34, along the channel 61 containing a restrictor 62 towards the thermally controlled valve 52.

The by-pass stream flows through the passage 56 leaving the valve 52 by means of a channel 64. The second by-pass stream then flows from channel 64 into passage 36 to rejoin the first stream prior to exit from the vaporiser 1 from the outlet 42.

A particular advantage of the embodiment described above is, that since the thermally controlled valve 52 is located immediately adjacent the other side of the base 50 of the sump 12 containing the liquid anaesthetic agent and selecting the material of the base so that it has a high thermal conductivity, the difference in temperature between the valve 52 and the liquid anaesthetic agent is very small even when the liquid anaesthetic agent temperature is changing rapidly. As a result of this, the change in anaesthetic drug concentration leaving the vaporiser 1 as the drug temperature changes is smaller than with contemporary vaporisers of the by-pass type.

A further important feature of the embodiment described above is that the valve 52 is easily accessible without releasing anaesthetic vapour into the atmosphere.

A third advantage of having the thermally control valve 52 located on the outside of the sump 12 is that adjustment of the passage 56 between the valve flapper 54 and the base 50 can be changed while gas is flowing through the vaporiser in the normal way with the concentration of the anaesthetic drug in the outlet 42 being measured. This feature enable an accurate calibration of the vaporiser to be performed with the adjustment being made until the measured output is at some desirable level coinciding with the output indicated on the vaporiser. This is normally the position of the knob 10 against some reference mark. The adjustment is made by turning the adjustment screw 58 by a screwdriver or other device inserted through the opening created when the plug 60 is withdrawn from the base 2 of the vaporiser 1. The design of the adjustment device may be such that when performing the adjustment it prevent gas escaping from the vaporiser through the hole left when the plug 60 is removed from the base 2.

Anaesthetic vaporisers in use are required to deliver an anaesthetic vapour laden gas having a concentration which is substantially constant for a given setting of the knob 10 even when the carrier gas flow rate into the vaporiser is varied. To meet this requirement with vaporisers of the by-pass type it is necessary to maintain the flow of anaesthetic vapour laden gas and the flow of by-pass carrier gas in a fixed proportion. This is achieved by having identical and linear flow resistance characteristics for each flow stream, that is, as the pressure difference between the point just before the flow split and just after the recombination point is changed a corresponding and equal change in the flow of each stream occurs.

In most known vaporisers of the by-pass type the main short-coming has been a fall off in delivered anaesthetic concentration as the fresh carrier gas flow to the vaporiser is increased. This has been particularly apparent at anaesthetic concentrations at or near the top of the available range, and is the result of a number of additional factors, such as variations in the degree of vapour pick-up which occur with flow rate etc.

By altering the flow split proportions such that at higher fresh carrier gas rates of flow into the vaporiser more gas passes through the sump, the anaesthetic agent output can be increased. This is done by increasing the flow resistance coefficient of the by-pass stream. The valve 52 is designed to have a linear flow characteristic and cannot perform this function. By adding a resistor 62 having a flow resistance characteristic independent of the valve 52 a greater degree of control of the drug output characteristic can be obtained. In particular, this restrictor 62 is designed to operate with turbulent flow such that the pressure difference across it increases with the square of the flow rate through it, it is more suited to act at the higher values of input flow to the vaporiser. Thus, at low flows its resistance value is very small compared with the valve 52 having virtually no effect on the anaesthetic agent output concentration from the vaporiser. As the flow increases, the restrictor's resistance value increases very much more rapidly than the valve 52 resistance and becomes significant enough at higher flow rates to increase the output of the vaporiser above that which is possible without the restrictor in place, and so maintain a more stable output concentration with flow variation.

The restrictor 62 is, as shown, located on the up stream side of the valve 52 so that the effect of the restrictor on output is present when the vaporiser is calibrated. However, the restrictor can be positioned on the downstream side of the valve 52.

The resistance characteristic of the restrictor may be selected to match the particular drug characteristics for which the vaporiser is to be used and so permit optimisation for each drug type.

We claim:

1. An anaesthetic vaporiser of the by-pass type in which carrier gas is initially divided into a first stream passing through a vaporising chamber containing volatile liquid anaesthetic agent thereby entraining vapour from the volatile liquid anaesthetic agent and a second by-pass stream, the two streams subsequently recombining prior to leaving the vaporiser for delivery to a patient, comprising a thermally responsive valve located in the second, by-pass stream, the vaporising chamber including a base made from a material with a high thermal conductivity, the thermally responsive valve being located immediately below the base in the normal orientation of the vaporiser.

2. An anaesthetic vaporiser as claimed in claim 1, in which a removable plug is located in a base of the vaporiser to give access to the thermally responsive valve.

3. An anaesthetic vaporiser as claimed in claim 1 or 2, in which a restrictor is placed in the second by-pass stream up-stream of the thermally responsive valve.

4. An anaesthetic vaporiser as claimed in claim 1 or 2, in which a restrictor is placed in the second by-pass stream down-stream of the thermally responsive valve.

5. An anaesthetic vaporiser of the by-pass type in which carrier gas is initially divided into a first stream passing through a vaporising chamber containing volatile liquid anaesthetic agent thereby entraining vapour from the volatile liquid anaesthetic agent, and a second by-pass stream; the two streams subsequently recombining prior to leaving the vaporiser for delivery to a patient, in which the vaporising chamber includes a base made from a material of high thermal conductivity, a thermally responsive valve being located in the second by-pass stream, and immediately below the base in the normal orientation of the vaporiser, and a restrictor placed in the second by-pass stream the restrictor having flow-pressure drop characteristics which are matched to a preselected anaesthetic agent requirement.

* * * * *